United States Patent
Quandt et al.

(10) Patent No.: US 8,338,311 B2
(45) Date of Patent: Dec. 25, 2012

(54) METHOD FOR THE PRODUCTION OF STRUCTURED LAYERS OF TITANIUM AND NICKEL

(75) Inventors: Eckhard Quandt, Heikendorf (DE); Clemens Schmutz, Köln (DE); Christiane Zamponi, Kiel (DE)

(73) Assignee: Acandis GmbH & Co. KG, Pfinztal (DE)

( * ) Notice: Subject to any disclaimer, the term of this patent is extended or adjusted under 35 U.S.C. 154(b) by 665 days.

(21) Appl. No.: 12/306,646

(22) PCT Filed: Jun. 27, 2007

(86) PCT No.: PCT/EP2007/005702
§ 371 (c)(1),
(2), (4) Date: Sep. 17, 2009

(87) PCT Pub. No.: WO2008/000467
PCT Pub. Date: Jan. 3, 2008

(65) Prior Publication Data
US 2010/0009142 A1    Jan. 14, 2010

(30) Foreign Application Priority Data
Jun. 27, 2006  (DE) .......................... 10 2006 029 831

(51) Int. Cl.
*H01L 21/302* (2006.01)
(52) U.S. Cl. .......... 438/754; 438/720; 438/758; 216/75; 216/77
(58) Field of Classification Search .................. 438/706, 438/714, 720, 745, 750, 754, 758, 737; 216/75, 216/77, 95, 102
See application file for complete search history.

(56) References Cited

U.S. PATENT DOCUMENTS

| | | | | |
|---|---|---|---|---|
| 3,742,317 | A * | 6/1973 | Shao | 257/484 |
| 6,791,233 | B2 * | 9/2004 | Tomonari et al. | 310/307 |
| 2004/0227427 | A1 * | 11/2004 | Pizzi et al. | 310/307 |
| 2005/0221529 | A1 * | 10/2005 | Bang et al. | 438/53 |
| 2007/0072396 | A1 * | 3/2007 | Feltin et al. | 438/478 |

FOREIGN PATENT DOCUMENTS
DE    669 20 712 T2    2/2006
(Continued)

OTHER PUBLICATIONS

Int'l Preliminary Report on Patentability and Written Opinion mailed on Jan. 22, 2009 in Int'l Application No. PCT/EP2007/005702.

(Continued)

*Primary Examiner* — Lan Vinh
(74) *Attorney, Agent, or Firm* — Pauly, DeVries, Smith & Deffner, L.L.C.

(57) ABSTRACT

A method for the production of a structured metal layer (7) made from an alloy composed of titanium and nickel includes the following process steps: a sacrificial layer composite (3) is provided, which comprises a second sacrificial layer (2) applied onto a first sacrificial layer (1), the first sacrificial layer (1) is subjected for the purpose of structuring to a wet-chemical etching process in such a manner that undercutting of the sacrificial layer (1) occurs, a metal layer (7) of the alloy is applied indirectly or directly to the structured sacrificial layer composite (3). The first sacrificial layer (1) is at a greater distance from the metal layer (7). The second sacrificial layer (2) facing the metal layer (7) to be deposited is subjected to a dry etching process prior to wet-chemical etching of the first sacrificial layer (1) so that the second sacrificial layer (2) is provided with a structure that corresponds to the desired structure of the metal layer (7). The invention further relates to an object, particularly a stent or an implant, which comprises at least one metal layer (7) that is produced by applying the method for the production of the structured metal layer (7).

24 Claims, 5 Drawing Sheets

FOREIGN PATENT DOCUMENTS

| | | |
|---|---|---|
| WO | 00/04204 A1 | 1/2000 |
| WO | 01/87371 A2 | 11/2001 |
| WO | 2004-008504 A1 | 1/2004 |

OTHER PUBLICATIONS

Lionel Buchaillot et al., "Thin Film of Titanium/Nickel Shape Memory Alloy for Multi-Degree of Freedom Microactuators", Seisan Kenkyu, vol. 51, No. 8, pp. 22-23, (1999).

Holger Rumpf et al., "Near Net-Shape Fabrication of Superelastic NiTi Devices by Sputtering and Photoetching", Materials Transactions, vol. 47, No. 3, pp. 523-526, (2006).

J. A. Walker et al., "Thin-film Processing of TiNi Shape Memory Alloy", Sensors and Actuators, A21, Nos. 1/3, pp. 243-246, (1990).

"Office Action from EP Application No. 07764894.7, mailed Jun. 27, 2012 corresponding to U.S. Appl. No. 12/306,646, pp. 1-5." (with English translation).

* cited by examiner

METHOD FOR THE PRODUCTION OF STRUCTURED LAYERS OF TITANIUM AND NICKEL

CROSS-REFERENCE TO RELATED APPLICATIONS

This application is a Section 371 of International Application No. PCT/EP2007/005702, filed Jun. 27, 2007, which was published in the German language on Jan. 3, 2008, under International Publication No. WO 2008/000467 A1 and the disclosure of which is incorporated herein by reference.

BACKGROUND OF THE INVENTION

The present invention relates to a method for the production of a structured metal layer made from an alloy composed of titanium and nickel.

Structured metal layers or metal foils produced in such a manner may be used in particular as a biocompatible implant, for example as embolic filters or as bands and generally as joining elements between the bones of the human skeleton. With appropriate shaping, such layers may also be used as stents in blood vessels. Thus the invention further relates to an object, particularly a stent or an implant, which comprises at least one layer produced according to this method.

The alloy with titanium and nickel used for the production of the metal layer advantageously has superelastic behaviour and/or shape memory properties. Materials with shape memory properties (SM materials) are characterized in particular in that they can be deformed in a low-temperature phase with martensite structure and after subsequent heating in a high-temperature phase with austenite structure they remember this impressed shape and return to it. A frequently used property of such materials is their superelastic behaviour. Within a specific time interval above a characteristic preload, which may be several hundred MPa, a plateau arises in the stress-strain curve. The austenite transforms into martensite within this strain range. The stress-induced martensite may decouple according to the stress applied and thus facilitates deformation of the material within the plateau under constant counterforce. At the same time, expansions up to approx. 8% may be introduced into the stress-induced martensite by way of the phase transformation without plastic deformation occurring. On relieving the load on the martensite, it transforms back to the initial condition of the austenite with a hysteresis with respect to the plateau stress.

Due to their good biocompatibility, materials made from nickel-titanium alloys (NiTi) are frequently used in medical technology. The superelastic properties of the nickel-titanium alloys are advantageous in medical tools such as catheters, which are used, for example, for stent positioning and which are exposed to severe deformations during their use in the body. Tissue spreaders with superelastic properties have the advantage that they cause less damage to the tissue than spreaders made from other materials. The shape memory effect may additionally be utilised in implants such as stents or embolic filters. In this case the implants are deformed in the martensitic state at room temperature. Subsequently, the deformed implants are inserted into the body where the high-temperature phase austenite is stable at body temperature. In the process, the implant transforms and remembers its original shape. The folded stents and embolic filters can thus unfold of their own accord.

Basically, the proportion of nickel in the alloy used for production of the metal layer may be varied within large limits between 2 and 98 atomic % depending on the application case. Preferably, however, it is suggested that the nickel content in the alloy should be between 45 and 60 atomic %.

Customarily, in implants, a compact material that is produced using conventional manufacturing techniques is used. It has, however, emerged that porous forms of the compact material are advantageous in medical implants since cells, particularly stem cells or bone cells, may in the process grow into the pores, thus ensuring better embedding of the implant in the bone or into the new tissue to be created. Thus, where stents and embolic filters are concerned, mesh-like structured shapes are also used. Typically, shaping of the stents is performed by means of a combination of deep drilling and laser cutting from solid material.

Furthermore, it is known to produce thin shape memory layers with a superelastic behaviour by means of physical deposition methods, especially by means of sputtering. At the same time, in addition to the advantage of using less material, sputtered layers of nickel-titanium alloys primarily enable the production of structures with smaller dimensions.

It is known, for the introduction of a structure into a layer of a nickel-titanium alloy sputtered as a closed surface, to subject the nickel-titanium layer to an etching process whereby photolithographic methods in particular may also be used. Lithographic structuring of nickel-titanium alloys is performed by means of a lithography step in which the desired structural shape is applied to a lacquer by means of masking. The light-sensitive lacquer is subsequently exposed and developed. The lacquer which is left behind in the process protects the regions of the structure, which should be retained, during further etching steps.

Nickel-titanium alloys may be etched wet-chemically using a hydrofluoric acid mixture (HF). The wet-chemical process is isotropic with the result that an undercut is also always produced in the process and the edge structure is adversely affected. In addition, undercutting, the level of which increases with thicker layers, also leads to the structural resolution being destroyed or the width of the ligands being lost. A further disadvantage exists in the etched surface remaining, which contains obvious signs of etching, with the result that if necessary a further surface treatment in the form of repolishing is needed. Furthermore, hydrogen may be introduced into the nickel-titanium alloys during chemical etching which may impair the shape memory properties or the superelastic properties.

Dry etching is another etching process in which the material to be removed from the nickel-titanium alloy is eroded or "sputtered" away by using an argon ion beam. This method is anisotropic with the result that there is no undercutting and the edge structures may be produced very cleanly. The method also prevents the introduction of hydrogen. One disadvantage of this method, however, is the low etching or erosion rate of just a few tenths of a nm/s which means considerable time expenditure. With layer thicknesses greater than 2 µm there is also the problem of redeposition where the material already eroded re-adheres to the surface.

In addition to these methods, by which the structure is not introduced into the metal layer until deposition has taken place, it is also known to introduce a structure into the substrate material onto which the nickel-titanium alloy layer will subsequently be deposited and which thus exists immediately in the desired structure.

Thus, using a method of the type referred to at the outset, which is known from International Patent Application Publication No. WO 00/04204 or from the corresponding German specification translation DE 699 20 712 T2, firstly a sacrificial layer composite is provided which comprises at least two sacrificial layers applied one on top of the other. One of these two sacrificial layers is subjected to a wet-chemical etching process for the provision of a structure during which undercutting of this sacrificial layer takes place. Subsequently, a metal layer of the alloy is applied indirectly or directly to the sacrificial layer composite already structured.

With this known method, the isotropic etching process gives rise to the disadvantages referred to above of signs of etching in the surface of the sacrificial layer which is etched wet-chemically. An especially smooth surface of the substrate or of a sacrificial layer used for deposition is, however, of major significance in achieving a high breaking strength of a sputtered nickel-titanium alloy. If crack nuclei in the shape of notches or pores are generated during layer production, then a material failure occurs in the tensile test at much lower stresses than the theoretical breaking strength. Local stress peaks, which exceed the breaking strength limit, are then reached in the material. Such stress peaks arise in notches, as represented by pores in the interior and scratches on the surface, due to a stress concentration.

BRIEF SUMMARY OF THE INVENTION

The object of the present invention is to have an easy to perform method of the type referred to at the outset with which structured nickel-titanium layers having high breaking strength can be produced particularly quickly and cost-effectively.

This object is achieved according to the invention by a process according to the present invention.

It is important in the solution according to the invention that the first sacrificial layer, which is at a greater distance from the metal layer to be deposited, is subjected to the wet-chemical etching process and that the second sacrificial layer facing the metal layer to be deposited is subjected to a dry etching process prior to wet-chemical etching of the first sacrificial layer, whereby it is provided with a structure that corresponds to the desired structure of the metal layer. In the process, the second sacrificial layer applied to the first sacrificial layer is advantageously removable from the first sacrificial layer by chemically selective means.

The main advantage here is that in this manner, due to an especially smooth surface of the sacrificial layer coming into contact with the eroded metal layer, a high-strength metal layer is achieved, and that despite this the areas required to be left clear in the sacrificial layer for the deposition of a structured metal layer can be achieved in a very short time in the required size.

Due to the combination according to the invention of the two etching methods referred to above and their carefully controlled application to two sacrificial layers, it is possible to utilize only the respective advantages which are primarily the speed of a wet-chemical process and the edge accuracy of an anisotropic dry-chemical etching process (IBE).

Thus a method is created with which structured metal layers or structured metal foils made from nickel-titanium alloys may be produced particularly easily, quickly and cost-effectively.

It is particularly advantageous if the metal layer is applied directly to the dry-etched second sacrificial layer. In this manner, the advantages of an especially smooth surface of the second sacrificial layer are better utilized with regard to optimum strength of the metal foil than if an intermediate layer is applied between the second sacrificial layer and the deposited metal layer.

To do this it is further suggested when using a lithographic process to subject the second sacrificial layer to the dry etching process, preferably after applying a photoresist which is structured by using a lithographic process into an etching mask corresponding to the desired structure of the metal foil, whereby the photoresist is removed from the second sacrificial layer prior to application of the metal layer. Thus the deposited metal layer comes into direct contact with the second sacrificial layer.

In this case, moreover, it is especially advantageous if wet-chemical etching of the first sacrificial layer takes place through the photoresist applied, the photoresist only being removed after wet-chemical etching of the first sacrificial layer. Thus the photoresist serves as an etching mask for both etching steps.

In order to achieve enhanced manageability, it is proposed to apply the sacrificial layer composite to a substrate prior to coating with the metal layer, which substrate may in particular be formed by a silicon wafer.

According to an especially preferred embodiment of the invention, it is provided that the first sacrificial layer has a thickness which is several times the thickness of the second sacrificial layer. In this manner, it is possible to etch sufficiently large cut-outs into the first sacrificial layer such that short-circuiting of the areas to be left clear, provided in the network structure of the metal foil, is safely prevented during sputtering.

Preferably, it is proposed for this that the first sacrificial layer have a thickness of more than 5 µm, in particular a thickness between 10 µm and 50 µm, and the second sacrificial layer have a thickness between 0.05 µm and 1 µm, in particular between 0.1 µm and 0.5 µm.

Preferably, the metal layer is deposited on the structured sacrificial layer composite by means of sputtering, in particular by means of magnetron sputtering.

In this case it is particularly favorable if the metal layer is applied in a thickness between 0.1 µm and 200 µm, in particular between 1 µm and 100 µm, and preferably between 5 g/m and 50 µm.

It may further be advantageous if at least one face layer is applied to the deposited metal layer, the face layer being composed of a material dissimilar to the alloy of the metal layer or being composed of an alloy dissimilar to the alloy.

According to an especially preferred embodiment of the invention, however, it is provided that at least one core layer is embedded in the metal layer, the core layer being composed of a material dissimilar to the alloy of the metal layer or being composed of an alloy dissimilar to the alloy. The core may, for example, be a magnetic material or even a material which has better X-ray visibility than nickel-titanium alloys. By completely embedding the core layer in the nickel-titanium layer, the biocompatibility of the metal layer is retained regardless of the material of the core layer, which is of major significance in medical technology.

Preferably, in this case, the face layer or core layer is also deposited, in particular by means of magnetron sputtering, on the metal layer which for its part is applied to the structured sacrificial layer composite.

It is favorable if the thickness of the face layer or core layer is only a fraction of the thickness of the metal layer. In this way, the additional layer(s) has/have only a minimal impact on the shape memory properties or the superelastic behaviour of the nickel-titanium layer.

For this purpose it is preferably proposed that the face layer or the core layer is applied in a thickness between 1 nm and 2 µm, in particular between 0.01 µm and 02 µm, and preferably between 0.02 µm and 0.1 µm.

It is particularly advantageous when embedding a core layer if the core layer is applied first of all to a first metal layer, whereby after this the core layer, in particular with the application of a photoresist structured lithographically into an etching mask, is subjected to an etching process, preferably a dry etching process, on some or preferably on all marginal areas, and subsequently, in addition to following the removal of a photoresist which may have been applied, a second metal layer is applied to the core layer and the first metal layer. In the process, the first and the second metal layer together form the nickel-titanium layer produced according to the invention. In this manner, complete coating of the core layer by the nickel-titanium alloy and thus biocompatibility are always guaranteed. In a simpler embodiment version of the method according to the invention, embedding of the core layer may, however, also take place without separate etching of the core layer margins.

According to a further especially preferred embodiment of the invention, the sacrificial layer composite is removed from the metal layer and/or dissolved after sputtering. In this manner, a self-supporting metal layer or a self-supporting film is obtained.

Moreover, it is especially advantageous if the metal layer is deposited as a three-dimensional body onto a three-dimensional, in particular cylindrical and rotating, sacrificial layer composite or is shaped and/or joined together into a three-dimensional body following planar deposition. Thus, a metal foil produced according to the invention, in particular after a substance-to-substance bond, for example after welding or sticking together into a tube, may be used as a stent.

The sacrificial layer composite may be applied to a cylindrical substrate for the creation of structures with a circular cross-section, in particular for the production of self-supporting stents produced by sputtering. In the process, a sacrificial layer disposed radially on the outside for the formation of a structure may be eroded, in particular etched, in certain areas corresponding to the structure of the metal layer to be produced. The sacrificial layer disposed radially on the outside provides the basis for assuming that it is possible to produce a supporting structure which has precisely fabricated edges and outlines. A photolithographic layer, which after exposure and development determines the structure according to the structure of the metal layer to be produced, may be applied to the sacrificial layer disposed radially on the outside to form the supporting structure. The use of a photolithographic process enables the formation of an etching mask on the sacrificial layer disposed radially on the outside, the mask meeting the requirements for the formation of a precise supporting structure. A dry etching process, in particular ion beam etching and/or reactive ion etching may be used to form the structure according to the structure of the metal layer to be produced. Such dry etching processes advantageously permit the formation of geometrically precise edges, which in subsequent process steps are reproduced in the structure of the metal layer upon coating the supporting layer with metal.

A sacrificial layer disposed radially on the inside may be eroded, in particular etched, in certain areas to form a structure according to the structure of the metal layer to be produced. The sacrificial layer disposed radially on the inside provides the basis for assuming that a sufficiently large quantity of material can be eroded from the sacrificial layer composite to enable the formation and separation of the self-supporting sputtered metal layer from the substrate. Breaking down of the sacrificial layer composite into a sacrificial layer disposed radially on the outside and a sacrificial layer disposed radially on the inside enables precision structuring firstly in the sacrificial layer disposed radially on the outside, which functions as the actual supporting layer for the metal coating, whereby the required erosion depth is achieved by etching or generally by erosion of the sacrificial layer disposed radially on the inside.

Thus a separation of function is effected by the sacrificial layer composite, whereby the sacrificial layer disposed radially on the outside is responsible for precision structuring and the sacrificial layer disposed radially on the inside is responsible for sufficient depth of erosion.

To form the structure according to the structure of the metal layer to be produced, it is possible to use a wet-chemical etching process which usually enables sufficiently high erosion rates that facilitates the desired erosion depth of the sacrificial layer disposed radially on the inside within a reasonable amount of time.

The photolithographic layer may be removed after processing of the sacrificial layers such that the metal layer can be applied, in particular, can be sputtered directly onto the sacrificial layer disposed radially on the outside.

The metal layer, in particular the nickel-titanium alloy, is advantageously applied at least to the sacrificial layer disposed radially on the outside. At the same time it is not ruled out that the metal layer may also be applied to the substrate due to structuring of the sacrificial layer disposed radially on the outside, which is particularly the case when coating by means of sputtering. Advantageously, the sacrificial layer composite is removed to form a self-supporting structured metal layer.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

First of all, the basic method for production of a thin-film nickel-titanium mesh represented schematically in FIGS. 1 to 7 is described in the following.

Figure 1:
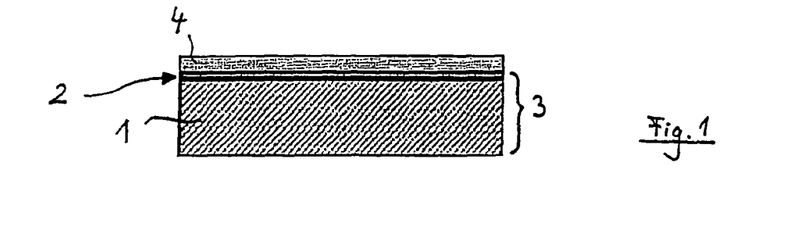
FIGS. 1 to 7 are diagrams which show a first embodiment of the production method according to the invention.

Firstly a first sacrificial layer 1 is deposited in a thickness of over 10 µm on a substrate which is not illustrated. Immediately on top of this is deposited a substantially thinner second sacrificial layer 2 of a material with a thickness of approx. 1 µm, which can be selectively removed chemically from sacrificial layer 1. Both sacrificial layers 1 and 2, which may, for example, be composed of gold, copper or chromium, together form a sacrificial layer composite 3, onto which the desired structure is then applied by means of a lithographic process. To do this, a photo lacquer layer 4 is applied first of all as a photoresist to upper sacrificial layer 2 (FIG. 1).

Figure 2:
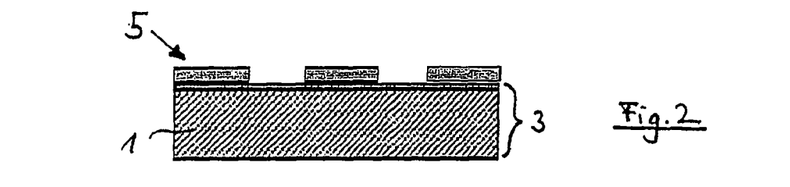

This photo lacquer layer 4 is then structured by applying a lithographic process using an appropriate lithography mask and an appropriate exposure source into a desired structure of the metal foil to be deposited according to etching mask 5 (FIG. 2).

Figure 3:
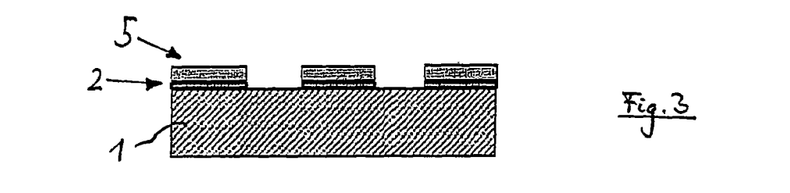

Subsequently, second sacrificial layer 2 situated on top is structured using etching mask 5 in a first etching step, which is performed as a dry etching process (FIG. 3).

Figure 4:
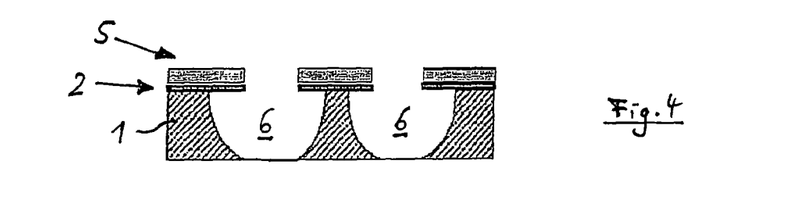

Following this, lower first sacrificial layer 1 is wet-chemically etched in a second etching step still using etching mask 5 and is removed down to the substrate forming areas to be left clear 6. At this juncture, intentional undercutting takes place, which is exploited in the further course of the process as an undercut below upper sacrificial layer 2 (FIG. 4).

Figure 5:
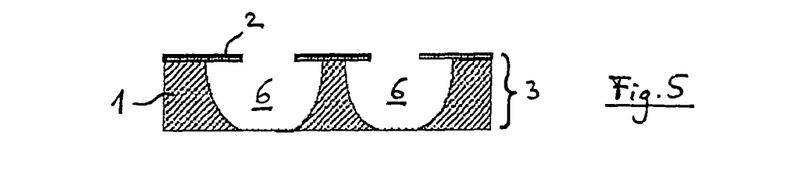

After completion of the two etching processes, etching mask 5 or the corresponding remains of photo lacquer 4 are removed, for example, by applying an acetone bath, such that finished pre-structured sacrificial layer composite 3 is left behind with desired areas to be left clear 6 in lower sacrificial layer 1 (FIG. 5).

Figure 6:
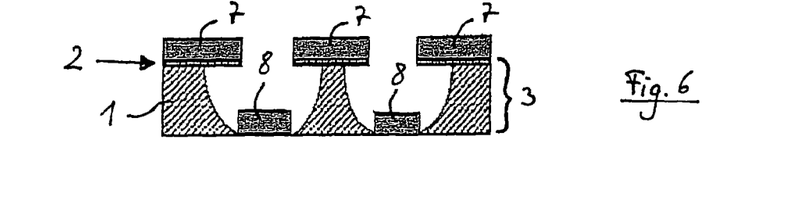

This is followed by the sputtering process, carried out here by means of cathode sputtering, in which the nickel-titanium alloy is deposited directly in a thickness of approx. 3 μm as structured metal layer 7 or as a structured metal foil onto the remaining residues of upper sacrificial layer 2 and is also deposited as a negative image 8 corresponding to the structure of metal layer 7 into areas to be left clear 6 in lower sacrificial layer 1 (FIG. 6). At the same time, microstructuring may also be achieved in addition by varying the process parameters, for example the sputter gas pressure during the sputtering process. The nickel content in the nickel-titanium alloy here is around 51 atom-%.

Figure 7:
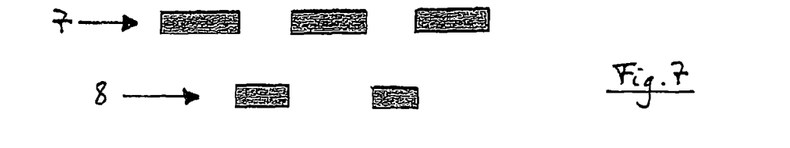
Figure 8:
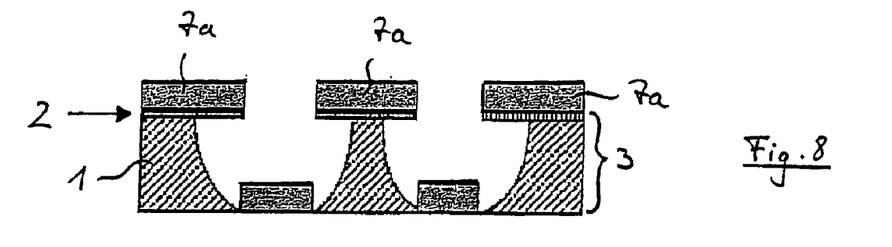
FIGS. 8 to 11 are diagrams which show a first variation of the production method illustrated in FIGS. 1 to 7.
Figure 9:
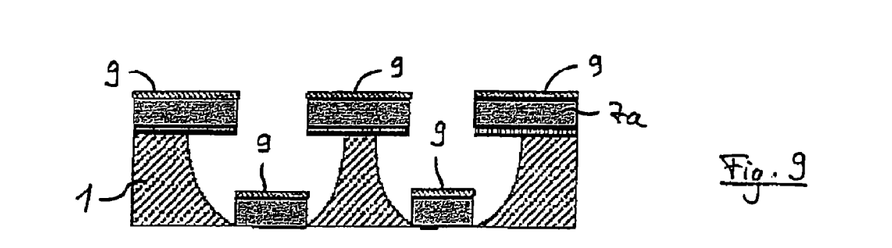

Finally, both sacrificial layers 1 and 2 are preferably dissolved in a chemical bath such that structured nickel-titanium alloy layer 7 is obtained as a self-supporting mesh structure (FIG. 7). This structured metal foil 7 produced according to the invention may be used advantageously, after appropriate shaping, in the medical field as an implant, particularly as a stent.

In the variation illustrated in FIGS. 8 to 11, a core layer 9 of a different metal alloy is embedded in structured metal foil 7 in order to achieve better X-ray visibility of a stent formed therefrom. To do this, a core layer 9 with a thickness of approx. 1 μm is likewise applied by sputtering (FIG. 9) to a first metal foil (7a) (FIG. 8) produced and initially deposited by the method of the kind previously described.

Figure 10:
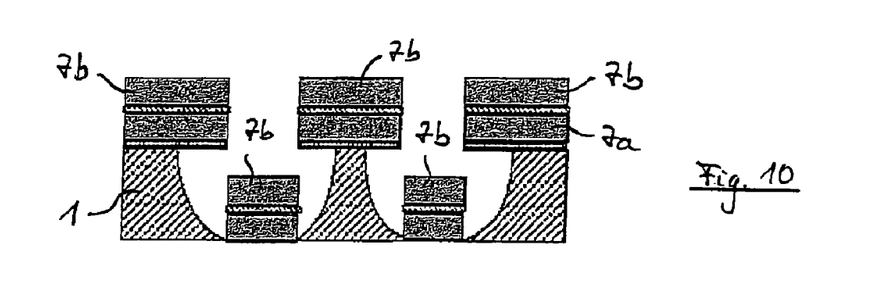
Figure 11:
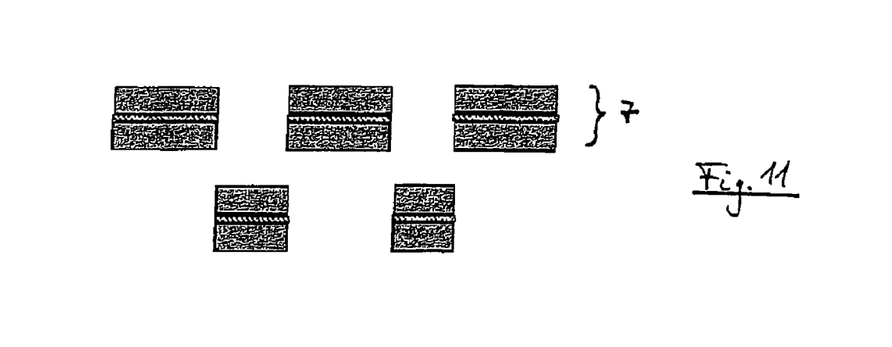
Figure 12:
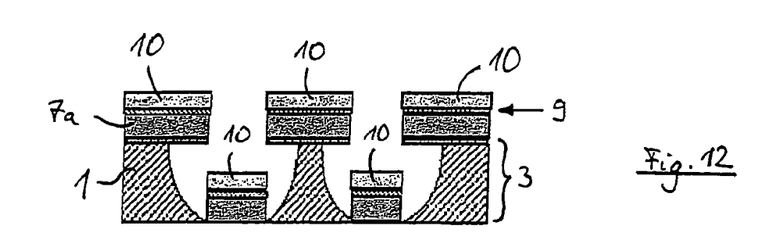
FIGS. 12 to 17 are diagrams which show a variation of the production method illustrated in FIGS. 8 to 10.

A second metal layer 7b is subsequently applied to core layer 9 (FIG. 10). After subsequent removal of both sacrificial layers 1, 2, first and second metal layer 7a, 7b together with core layer 9 sandwiched between them form a nickel-titanium metal layer 7 produced according to the method according to the invention (FIG. 11).

Figure 13:
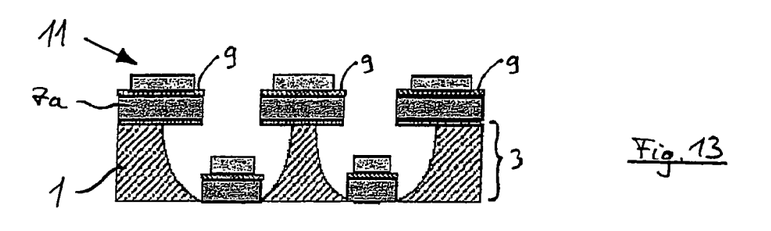

The modification illustrated in FIGS. 12 to 17 is proposed in order to obtain complete embedding of core layer 9 in nickel-titanium layer 7 for the purpose of improved biocompatibility. Proceeding from the intermediate step illustrated in FIG. 9, applied firstly to core layer 9 is a photo lacquer layer 10 (FIG. 12), which as a photoresist is likewise structured into an etching mask 11 by means of lithographic methods including exposure and developing (FIG. 13).

Figure 14:
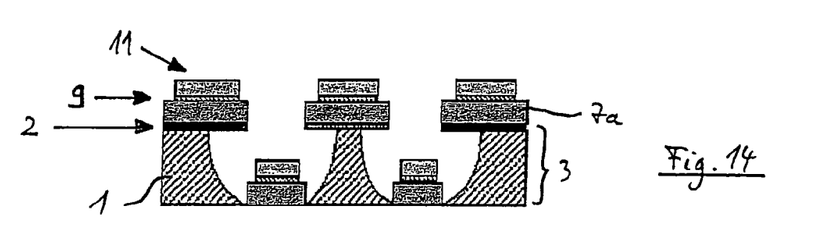
Figure 15:
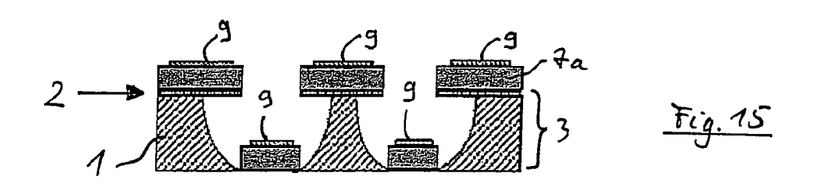

Subsequently, core layer 9 is etched on its marginal areas, using etching mask 11 produced beforehand, in a dry etching process, which is performed here for example by means of reactive ion etching (RIE) (FIG. 14). In this case, all margins of core layer 9 are etched away in an area that is somewhat larger than the thickness of core layer 9.

Figure 16:
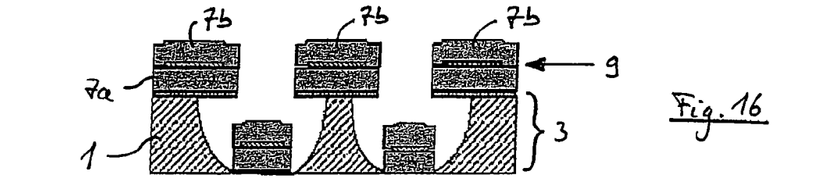

Thereafter, etching mask 11 is removed preferably by using an acetone bath (FIG. 15) and subsequently second metal layer 7b is sputtered onto core layer 9 as well as onto the now exposed marginal areas of first metal layer 7a (FIG. 16).

Figure 17:
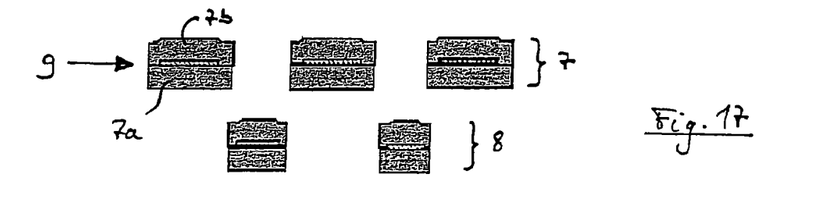

It can be seen in this case that core layer 9 is also completely surrounded on its margins by both metal layers 7a, 7b which, after final removal of both sacrificial layers 1, 2, in turn together with sputtered core layer 9 sandwiched therebetween form nickel-titanium metal layer 7 produced in line with the method according to the invention (FIG. 17).

FIGS. 18 to 28 are diagrams which show a second embodiment of the invention, which is provided in particular for the production of self-supporting metal layers 7 having three-dimensional, i.e. non-planar, structures. The second embodiment is particularly suitable for the production of self-supporting stents which are produced by sputtering or other coating techniques. Unlike conventional stents which, for example, have a sputtered coating, the stents producible using the method described below have no supporting structure and are rather constructed completely from a lattice structure that is created by sputtering.

In this case, use is made of the previously described principle according to the invention, in which a sacrificial layer composite 3 is used to form a structured supporting layer for subsequent coating with the stent material. Sacrificial layer composite 3 comprises at least two sacrificial layers 1, 2 which are subjected to fine structuring and coarse structuring. During fine structuring, a structure is formed which corresponds to the structure of metal layer 7 to be produced and which is produced with a high level of precision. A low erosion depth is sufficient for this with the result that sacrificial layer 2 provided for fine structuring may be correspondingly thin. For the formation of a sufficient wall thickness of the stent or generally of structured metal layer 7, it is necessary for the erosion depth of sacrificial layer composite 3 to be greater than the erosion depth used for fine structuring. A different erosion method, which enables correspondingly high erosion rates, is applied to sacrificial layer 1 in order to achieve the erosion depth required.

The core of the invention thus consists of specifying a method for the production of structured metal layers 7, in particular for the production of stents, wherein a sacrificial layer composite 3 with at least two sacrificial layers 1, 2 is used, the sacrificial layers being structured using different erosion methods, whereby one sacrificial layer 2 is finely structured by means of an erosion method with a low erosion rate and other sacrificial layer 1 is coarsely structured using an erosion method with a high erosion rate.

Figure 18:
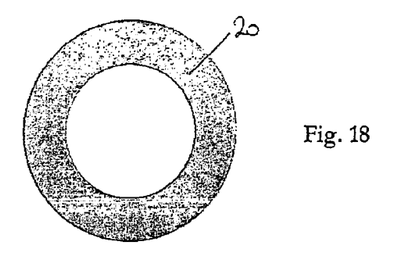
FIGS. 18 to 28 are diagrams which show a second embodiment of the production method according to the invention.

For the production of self-supporting sputtered stents, a substrate 20 with a circular cross-section is used, for example a hollow cylindrical or solid cylindrical substrate 20. Substrate 20 may be made of glass or metal, for example, of copper (FIG. 18).

Figure 19:
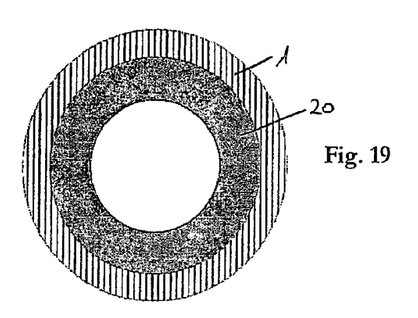

Sacrificial composite layer 3 is applied or deposited onto substrate 20. To do this, firstly a sacrificial layer 1 is deposited directly onto substrate 20, the sacrificial layer being disposed radially on the inside in sacrificial layer composite 3 and forming a first sacrificial layer 1 (FIG. 19). On first sacrificial layer 1 is deposited a second sacrificial layer 2, which is disposed radially on the outside in sacrificial layer composite 3. This means that first sacrificial layer 1 is disposed between substrate 20 and sacrificial layer 2 disposed on the outside (FIG. 20).

At the same time it is not ruled out that further sacrificial layers are provided.

Figure 20:
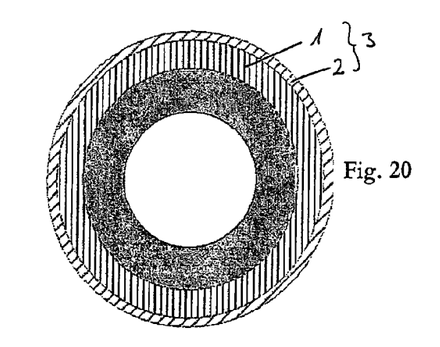

It can clearly be seen in FIG. 20 that second sacrificial layer 2 disposed radially on the outside has a smaller wall thickness than first sacrificial layer 1 disposed radially on the inside. The wall thickness of sacrificial layer 2 disposed radially on the outside corresponds approximately to the wall thickness of the self-supporting stent to be produced. The wall thickness of first sacrificial layer 1 disposed radially on the inside corresponds at least to the wall thickness of second sacrificial layer 2 disposed radially on the outside. In particular, the ratio of the wall thickness of second sacrificial layer 2 disposed radially on the outside to the wall thickness of first sacrificial layer 1 disposed radially on the inside ranges from 1:1 to 1:5, in particular 1:2 to 1:4.

Figure 21:
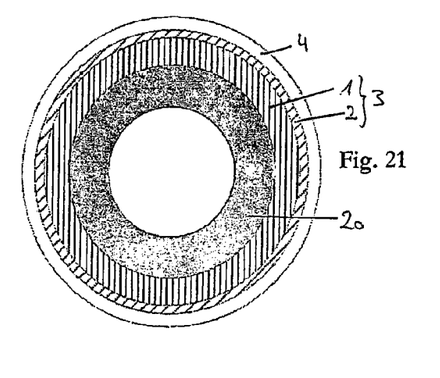
Figure 22:
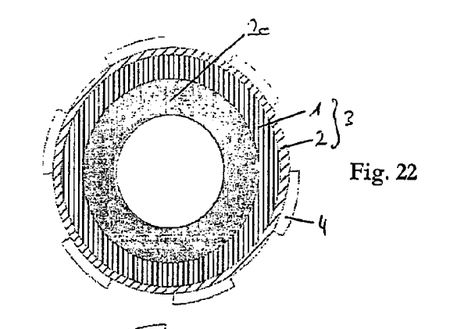
Figure 23:
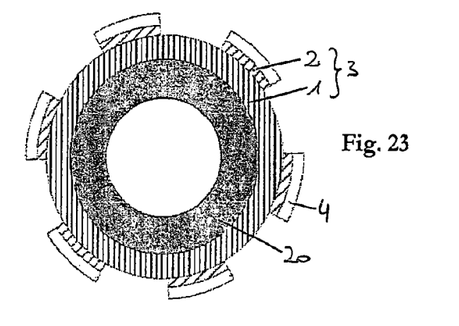

A photolithographic coating 4 or a photo lacquer or photo resist is applied to sacrificial layer 2 disposed radially on the outside (FIG. 21). To form an etching mask 5, photolithographic layer 4 is exposed and developed, whereby etching mask 5 produced as a result corresponds to the structure, in particular the lattice structure, of metal layer 7 to be produced or of the self-supporting stent to be produced (FIG. 22).

After creation of the etching mask (FIG. 22), second sacrificial layer 2 disposed radially on the outside is finely structured, whereby a structure of second sacrificial layer 2 corresponding to the etching mask is produced. For this purpose, an erosion method, in particular an etching method, is used which enables appropriate fine structuring, in particular the formation of geometrically precise edges without appreciable undercuts occurring. The etching process used for fine structuring may have a comparatively low erosion rate without the production process being delayed thereby since coarse structuring or the generation of an adequate erosion depth is achieved in a further process step by means of a different erosion method (FIG. 24).

A dry-etching process, in particular ion beam etching (IBE) and/or reactive ion etching (RIE), is used for fine structuring of sacrificial layer 2 disposed radially on the outside. Other erosion methods, which enable precise fine structuring, may likewise be used.

Figure 24:
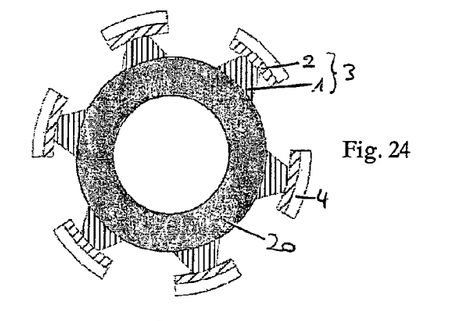
Figure 25:
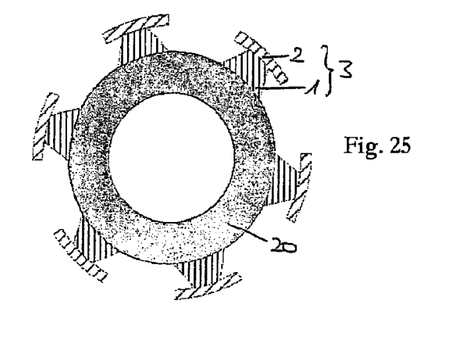

The necessary etching or erosion depth is achieved by applying a different erosion method or etching method to thicker first sacrificial layer 1 disposed on the inside (FIG. 24). In this case, a method is used which has a correspondingly high erosion or etching rate, for example, a wet-chemical etching process. The undercuts arising in the process or creation of the coarse edge structure in the region of first sacrificial layer 1 disposed radially on the inside are harmless since second sacrificial layer 2 disposed radially on the outside, which is responsible for reproduction of the lattice structure of metal layer 7 or of the stent to be produced, is finely structured and is not affected by coarse structuring of sacrificial layer 1 disposed radially on the inside. After both fine structuring (FIG. 23) and also coarse structuring (FIG. 24) are complete, photolithographic layer 4 may be removed (FIG. 25) so that finely structured sacrificial layer 2 disposed radially on the outside is exposed for subsequent metal coating.

Figure 26:
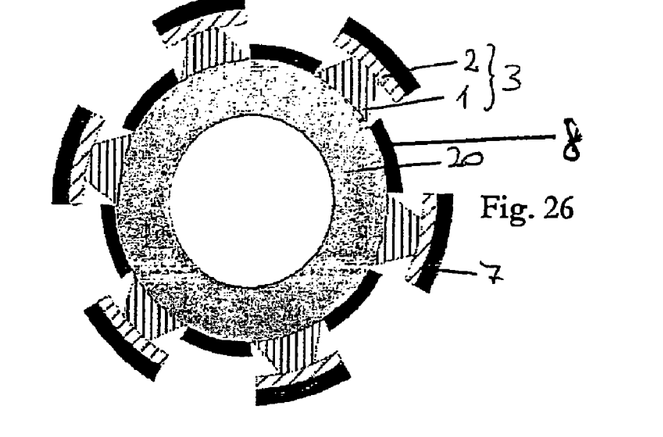
Figure 27:
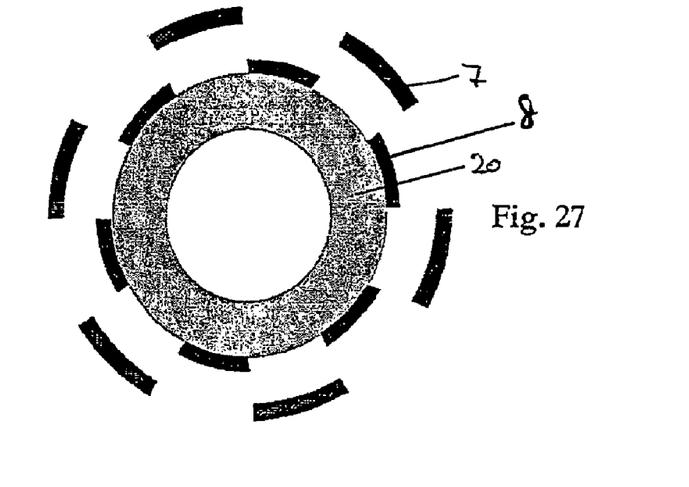

Coating of structured sacrificial layer composite 3 with the stent material takes place subsequently. Coating is carried out by means of a common coating method, preferably by means of sputtering. Other PVD or CVD methods (physical vapour deposition/chemical vapour deposition) are possible for application of the stent material to second sacrificial layer 2 disposed radially on the outside. The geometrically precise edges formed on fine structuring of sacrificial layer 2 disposed radially on the outside or in general the geometrically precise outline of the structured supporting layer is reproduced on the structure of metal layer 7. In this way it is possible to produce a precisely shaped lattice structure of the stent by means of a coating method, in particular by means of sputtering (FIG. 26). As also illustrated in FIG. 26, stent material 8 is deposited on substrate 20 in the open spaces between the coated supporting structures or in coated sacrificial layer composite 3. Stent material 8 deposited directly on substrate 20 thus forms a negative mould of material 7 deposited on sacrificial layer composite 3 or of material layer 7. Coarsely structured, relatively thick, first sacrificial layer 1 is dimensioned such that a sufficient gap is provided between metal layer 7 deposited on finely structured sacrificial layer 2 and stent material 8 deposited on substrate 20 so as to prevent the existence of joints or bridges between metal layer 7 and stent material 8 deposited directly on substrate 20.

Figure 28:
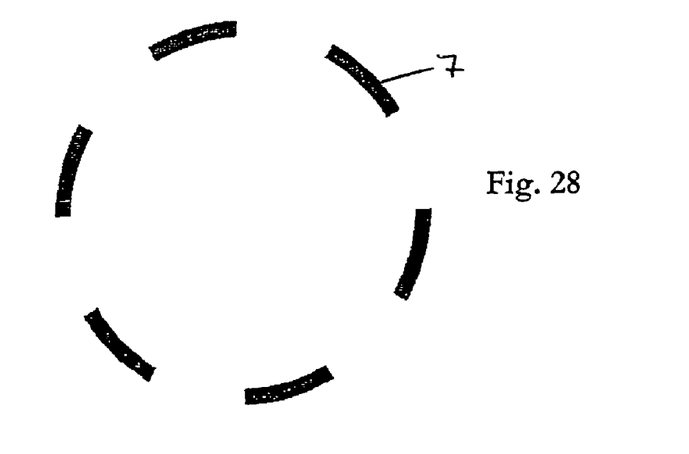

To release the self-supporting stent or generally self-supporting structured metal layer 7, sacrificial layer composite 3 is removed, in particular completely by means of etching. As a result, structured metal layer 7 or the self-supporting stent comes clear of substrate 20 and can simply be peeled off (FIG. 28).

The method described above is particularly suited to the production of self-supporting, sputtered stents. The method may also be transferred to other non-planar structures, whereby the substrate is correspondingly adapted for the application or creation of the sacrificial layer composite. The method is thus very flexible and provides the basic requirement for the production of different geometrical structures. All features, which are disclosed in connection with the second embodiment, will also be disclosed, insofar as technically feasible, in connection with the other embodiments and vice versa.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A method for the production of a self-supporting structured metal layer comprising an alloy comprising titanium and nickel, the method comprising the following process steps:
   providing a sacrificial layer composite, the sacrificial layer composite comprising a second sacrificial layer applied onto a first sacrificial layer;
   subjecting the second sacrificial layer to a dry etching process;
   subjecting the first sacrificial layer to a wet-chemical etching process such that undercutting of the first sacrificial layer occurs, wherein the subjecting of the first sacrificial layer to the wet-chemical etching process occurs after the subjecting of the second sacrificial layer to the dry etching process;
   applying the metal layer of the alloy to the sacrificial layer composite; and
   removing the first and second sacrificial layers to form a self-supporting structured metal layer.

2. The method according to claim 1, wherein the applying of the metal layer comprises applying the metal layer to the dry-etched second sacrificial layer.

3. The method according to claim 1, wherein the providing of the sacrificial layer composite comprises applying the sacrificial layer composite (to a substrate.

4. The method according to claim 1, wherein the applying of the metal layer to the sacrificial layer composite comprises sputtering.

5. The method according to claim 1, wherein the metal layer has a thickness between 0.1 pm and 200 pm.

6. The method according to claim 1, wherein the applying of the metal layer comprises depositing the metal layer as a three-dimensional body onto a three-dimensional sacrificial layer composite or comprises shaping or joining together the metal layer into a three-dimensional body.

7. An object produced according to the method of claim 1, comprising at least one metal layer.

8. The method according to claim 1, further comprising applying a photoresist to the second sacrificial layer, the photoresist being structured with a lithographic process into an etching mask corresponding to the structure of the metal layer, wherein the subjecting of the second sacrificial layer to the dry etching process occurs after the applying of the photoresist, the method further comprising removing the etching mask from the second sacrificial layer prior to the applying of the metal layer.

9. The method according to claim 8, wherein the removing of the etching mask takes place after the subjecting of the first sacrificial layer to the wet-chemical etching process.

10. The method according to claim 1, wherein the first sacrificial layer has a thickness which is several times a thickness of the second sacrificial layer.

11. The method according to claim 10, wherein the first sacrificial layer has a thickness of more than 5 pm and the second sacrificial layer has a thickness between 0.05 pm and 1 pm.

12. Method according to claim 1, further comprising embedding at least one core layer in the metal layer, the core layer being composed of a material or alloy dissimilar to the alloy of the metal layer.

13. The method according to claim 12, wherein applying the metal layer comprises applying a first metal layer applying a core layer on the first metal layer, subjecting the core layer to an etching process, and applying a second metal layer to the core layer and the first metal layer.

14. The method according to claim 1, further comprising applying at least one face layer to the metal layer, the face layer being composed of a material or alloy dissimilar to the alloy of the metal layer.

15. The method according to claim 14, wherein the applying of the at least one face layer comprises sputtering.

16. The method according to claim 14, wherein the thickness of the face layer is a fraction of the thickness of the metal layer.

17. The method according to claim 16, wherein the face layer has a thickness between 1 nm and 2 pm.

18. The method according to claim 1, wherein the providing of the sacrificial layer composite comprises applying the sacrificial layer composite to a cylindrical substrate.

19. The method according to claim 18, wherein the second sacrificial layer is disposed radially as an outside of the sacrificial layer composite.

20. The method according to claim 19, wherein the applying of the metal layer comprises applying the metal layer to at least the second sacrificial layer.

21. The method according to claim 1, further comprising removing the sacrificial layer composite to create a self-supporting structured metal layer.

22. The method according to claim 19, further comprising applying a photolithographic layer to the second sacrificial layer and exposing and developing the photolithographic layer.

23. The method according to claim 22, further comprising removing the photolithographic layer after the etching of the first and second sacrificial layers.

24. A method for the production of a self-supporting structured metal layer, comprising structuring a supporting layer comprising a sacrificial layer composite, the sacrificial layer composite comprising at least a first and a second sacrificial layer, wherein in a first step the second sacrificial layer is finely structured and in a second step the first sacrificial layer is coarsely structured, the method further comprising depositing a metal layer on the finely structured sacrificial layer, and subsequently removing the first and second sacrificial layers to leave a self-supporting structured metal layer.

* * * * *